United States Patent [19]

Jakubowski

[11] Patent Number: 5,421,353

[45] Date of Patent: Jun. 6, 1995

[54] ULTRASONIC DENTURE CLEANING SYSTEM

[76] Inventor: Henryk P. Jakubowski, 65-10 108 St. Apt. 5H, Forest Hills, N.Y. 11375

[21] Appl. No.: 185,474

[22] Filed: Jan. 24, 1994

[51] Int. Cl.⁶ ............................................. B08B 3/12
[52] U.S. Cl. .................... 134/58 R; 134/95.1; 134/104.2; 134/186
[58] Field of Search .................. 134/1, 26, 58 R, 95.1, 134/184, 186, 104.2, 104.4

[56] References Cited

U.S. PATENT DOCUMENTS

| | | | |
|---|---|---|---|
| 2,728,562 | 12/1955 | Bailey . | |
| 3,024,138 | 3/1962 | Schlott | 134/1 |
| 3,141,467 | 7/1964 | Robson | 134/95.1 X |
| 3,151,846 | 10/1964 | George | 134/184 X |
| 3,380,446 | 4/1968 | Martin . | |
| 3,386,706 | 6/1968 | Leifman et al. . | |
| 3,399,869 | 9/1968 | Loria et al. | 134/184 X |
| 3,516,861 | 6/1970 | Menkes et al. | 134/26 X |
| 3,580,261 | 5/1971 | Key | 134/104.4 |
| 4,129,456 | 12/1978 | Longo | 134/1 |
| 4,409,999 | 10/1983 | Pedziwiatr | 134/184 X |
| 4,710,233 | 12/1987 | Hohmann et al. | 134/1 |
| 4,870,982 | 10/1989 | Liu | 134/184 X |
| 5,113,881 | 5/1992 | Lin et al. | 134/1 |
| 5,201,958 | 4/1993 | Breunsbach et al. | 134/95.1 X |

FOREIGN PATENT DOCUMENTS

| | | | |
|---|---|---|---|
| 3633046 | 1/1988 | Germany | 134/184 |
| 226586 | 9/1989 | Japan | 134/1 |
| 1416979 | 12/1975 | United Kingdom | 134/184 |

*Primary Examiner*—Philip R. Coe
*Attorney, Agent, or Firm*—Collard & Roe

[57] ABSTRACT

A method and apparatus for cleaning an object in a cleaning solution and then rinsing the object in a rinse solution. The apparatus includes a cleaning tank with an inlet valve and an outlet valve. The object to be cleaned and the cleaning solution are placed into the cleaning tank. An ultrasonic transducer generates ultrasonic vibrations in the cleaning solution. A controller maintains the object immersed in the cleaning solution for a first period of time and then generates ultrasonic vibrations for a second period of time. The outlet valve is then opened to drain the cleaning solution from the tank. The inlet valve is subsequently opened to fill the cleaning tank with rinse solution. The apparatus is particularly suited for cleaning dentures with the rinse solution and the cleaning solution being selected to properly hydrate acrylic denture material and soft re-line materials.

7 Claims, 2 Drawing Sheets

5,421,353

ULTRASONIC DENTURE CLEANING SYSTEM

BACKGROUND OF THE INVENTION

1. Field of the Invention

The present invention relates to a method and apparatus for cleaning and rinsing dentures. More specifically, it relates to a method and apparatus for ultrasonically cleaning dentures and thereafter rinsing off the cleaning solution.

2. The Prior Art

It is known to use chemical, mechanical or vibratory means to clean objects immersed within a liquid solution. Ideally, a particular cleaning solution is selected in conjunction with mechanical or vibratory means to cooperatively clean objects. Certain cleaning methods are set forth in the following U.S. patents: U.S. Pat. No. 2,728,562 to Bailey, U.S. Pat. No. 3,380,446 to Martin, U.S. Pat. No. 3,386,706 to Leifman et al, U.S. Pat. No. 3,399,869 to Loria, U.S. Pat. No. 4,129,456 to Longo, U.S. Pat. No. 4,870,982 and U.S. Pat. No. 5,113,881. However, these patents do not disclose the preferred method for cleaning dentures.

Ideally, dentures are soaked in a mild acidic cleaning solution and then subjected to ultrasonic vibrations. However, a drawback exists with this cleaning method, as the mild acidic cleaning solution needs to be rinsed from the dentures before use. Because of the obvious safety implications from failing to rinse the acidic cleaning solution, this preferred cleaning method has not been heretofore made available for home use. Therefore, it would be desirable to provide a method and apparatus for chemically and ultrasonically cleaning dentures and subsequently rinsing the chemical agent from the dentures.

SUMMARY OF THE INVENTION

It is the purpose of the invention to overcome the drawbacks of the prior art and to provide a method and apparatus for readily and safely cleaning dentures in the home.

It is a further object of the present invention to provide a method and apparatus in which the dentures are immersed in a mild acidic cleaning solution and subjected to ultrasonic vibrations.

It is a further object of the present invention to provide a method and apparatus for cleaning dentures in which the acidic cleaning solution is drained from the cleaning tank automatically.

It is yet another object of the present invention to provide a method and apparatus for cleaning dentures in which the acidic cleaning solution is rinsed from the dentures.

It is a further object of the present invention to provide a method and apparatus for cleaning dentures that includes a cycle selection control which automatically coordinates operation of the denture cleaning apparatus.

These and other related objects are achieved according to the invention by a method for cleaning and rinsing an object, including the steps of placing the object and a cleaning solution into a tank and soaking the object for a first predetermined period of time. Ultrasonic vibrations are then generated in the cleaning solution for a second predetermined period of time and the cleaning solution is then drained from the tank. The object is rinsed with a rinse solution and the cleaned and rinsed object is removed from the tank.

A cleaning cycle with a first and second predetermined period of time is selected prior to soaking the object. The first and second predetermined periods of time are selected based on the object to be cleaned. When cleaning dentures, the cleaning solution is selected from a group consisting of a mild acidic cleaning solution, a disinfectant and a detergent. The cleaning cycle is selected as an overnight cycle or a short cycle lasting less than one hour.

In a further embodiment, the invention consists of an apparatus for cleaning an object in a cleaning solution and rinsing the object in a rinse solution. The apparatus includes a cleaning tank adapted to receive the object and the cleaning solution. The cleaning tank has an inlet valve and an outlet valve. An ultrasonic transducer is coupled to the cleaning tank for generating ultrasonic vibrations in the cleaning solution. A controller, including timing means, is coupled to the inlet valve, the outlet valve and the ultrasonic transducer. The timing means determines a first period of time for maintaining the object immersed in the cleaning solution and a second period of time for generating ultrasonic vibrations. The controller thereafter opens the outlet valve to drain the cleaning solution from the tank and then closes the outlet valve. The controller subsequently opens the inlet valve to fill the cleaning tank with the rinse solution.

The apparatus further includes a storage tank coupled to the inlet valve for storing the rinse solution. A waste tank is coupled to the outlet valve for receiving the cleaning solution drained from the cleaning tank. The cleaning solution is selected from a group consisting of a mild acidic cleaning solution, a disinfectant and a detergent. The cleaning tank has a cleaning tank lid and a lock for locking the lid in a closed position. The lock is coupled to the controller, whereby the controller keeps the lid locked until the cleaning tank is filled with the rinse solution. The rinse solution and the cleaning solution are selected to properly hydrate acrylic denture material and soft reline materials. The controller consists of a microprocessor having input means for selecting different cleaning and rinse cycles.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views:

FIG. 3 is a basket for use with the apparatus of FIG. 1.

DETAILED DESCRIPTION OF THE PREFERRED EMBODIMENT

Figure 1:
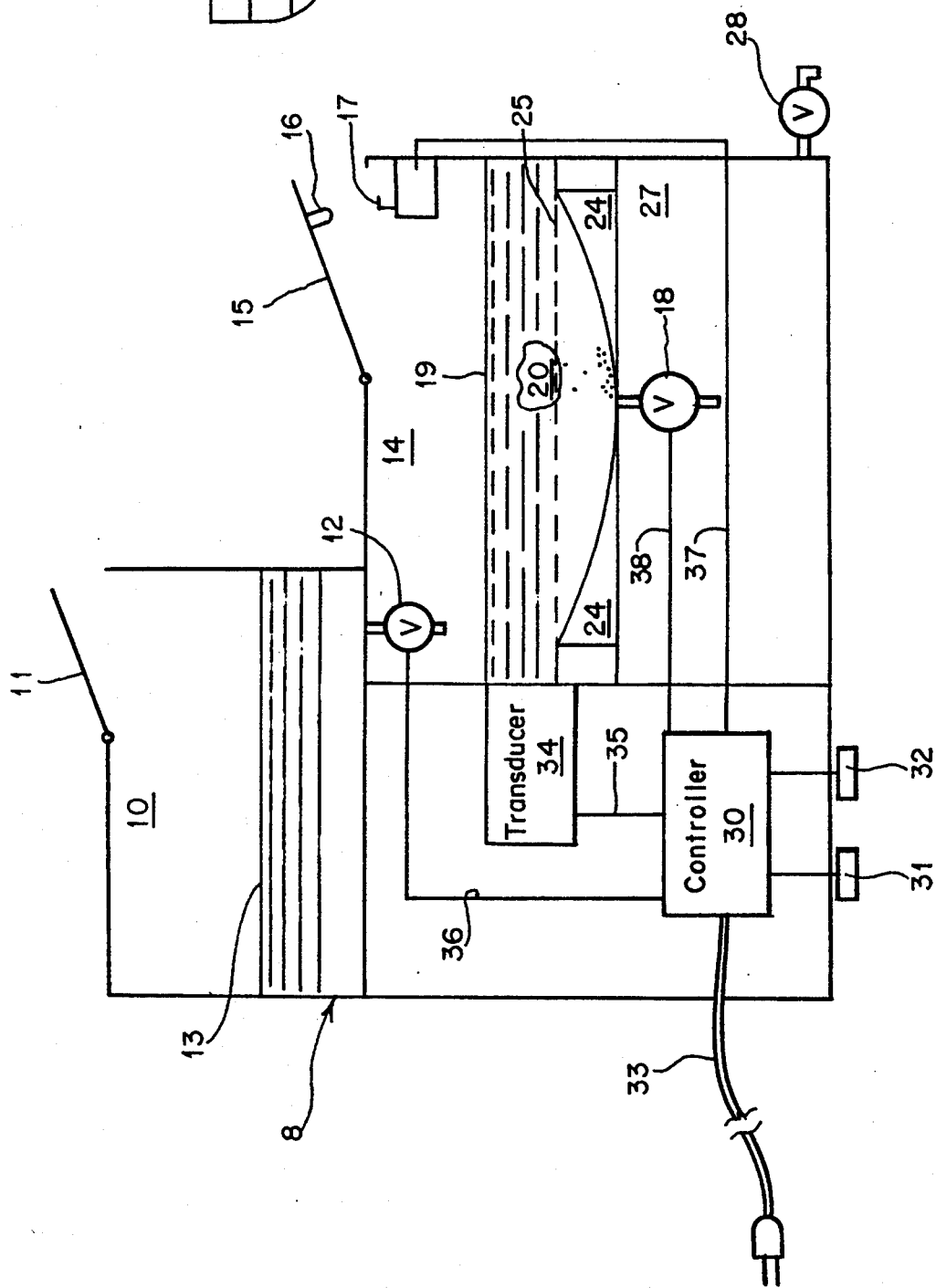
FIG. 1 is a schematic drawing of an embodiment of the apparatus for cleaning dentures according to the invention.

Referring now in detail to the drawings, and in particular FIG. 1, there is shown a denture cleaning apparatus 8, including a rinse solution tank 10, a rinse solution tank cover 11, and a rinse solution tank valve 12. Rinse solution tank 10 contains a rinse solution 13 that is poured into tank 10 through an opening under cover 11.

A cleaning tank 14 is disposed generally below valve 12 so that rinse solution 13 can be drained into cleaning tank 14. Cleaning tank 14 includes a cleaning tank cover 15 equipped with a cleaning tank cover latch 16. A cleaning tank locking pin 17 is provided for releasably engaging latch 16. Cleaning tank 14 contains a cleaning solution 19 and an object to be cleaned 20, both of which are placed into cleaning tank 14 through an opening under cover 15. The bottom of cleaning tank 14 includes a cleaning tank valve 18 and a drain plate 24, which is sloped toward valve 18. A screen 25 rests on top of drain plate 24 to raise object 20 off of drain plate 24.

A waste tank 27 is disposed generally below cleaning tank 14, so that cleaning solution 19 can be drained into waste tank 27. Waste tank 27 is equipped with a waste tank valve 28 for draining solution from waste tank 27. Alternatively, waste tank 27 is a drawer-type sliding tank that is removable to empty the fluid contained therein.

A controller 30 is provided with user operated cycle selectors 31 and 32. A power cord 33 provides power to controller 30. An ultrasonic transducer 34 is coupled to cleaning tank 14 and is connected to controller 30 through ultrasonic transducer control line 35. Valve 12 is connected to controller 30 through rinse solution tank valve control line 36. Cleaning tank locking pin 17 is connected to controller 30 through cleaning tank lock control line 37. Cleaning tank valve 18 is connected to controller 30 through cleaning tank valve control line 38.

Figure 2:
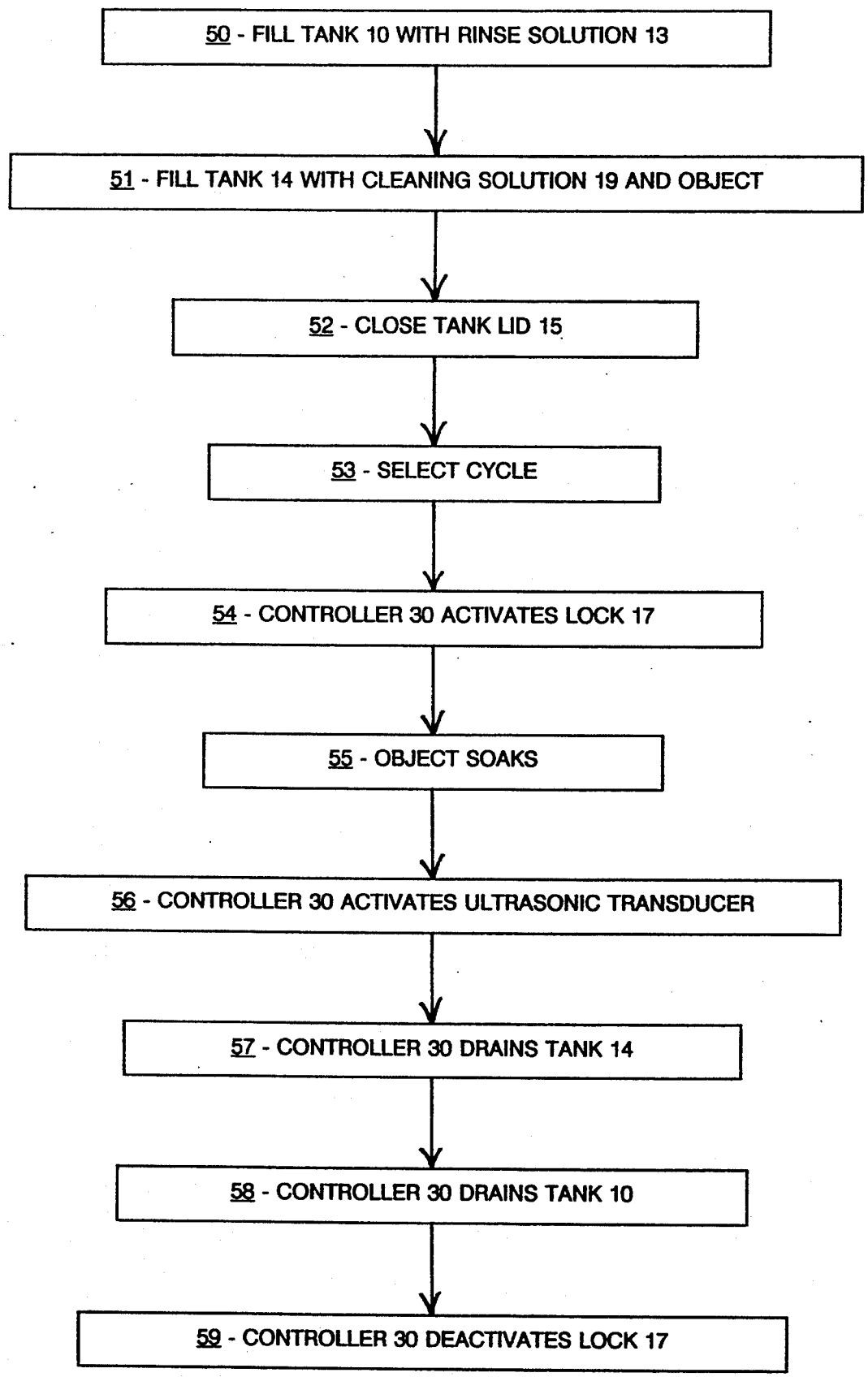
FIG. 2 is a flow chart showing the various operational steps of the denture cleaning apparatus.

Cleaning apparatus 8 operates in accordance with the flow chart shown in FIG. 2. Initially, in step 50, rinse solution tank 10 is filled with rinse solution 13 through the opening under cover 11. In step 51, cleaning tank 14 is filled with cleaning solution 19 and the object to be cleaned 20. At this point, any waste liquid in waste tank 27, could be manually drained through waste tank valve 28. However, waste tank 27 ideally holds waste liquid generated during numerous cleaning cycles so that it need only be emptied once a week, for example.

In step 52, cleaning tank cover 15 is closed. In step 53, the user depresses cycle selector 31 or 32 to select a fast cleaning cycle or an overnight cycle, for example. Additional cycles may also be provided. The timing sequence for each cycle may be stored in a ROM chip. Following selection of a particular cycle, controller 30 which includes a microprocessor, accesses the ROM chip associated with the cycle selected. The timing sequence stored in that ROM chip then programs the microprocessor to soak the object, generate ultrasonic vibrations, open and close valves, etc.

In step 54, controller 30 activates locking pin 17 via cleaning tank lock control line 37. In step 55, object 20 is soaked in cleaning solution 19 for a first predetermined period of time based on the selected cycle.

In step 56, controller 30 activates ultrasonic transducer 34 for a second predetermined period of time, also based on the cycle selected. Object 20 may be alternately soaked and subjected to ultrasonic vibrations numerous times. In step 57, controller 30 drains cleaning solution 19 from cleaning tank 14 by opening cleaning tank valve 18 via cleaning tank valve control line 38. Cleaning tank valve 18 is then closed. In step 58, controller 30 drains rinse solution tank 10 by opening rinse solution tank valve 12 via rinse solution tank valve control line 36. The rinse solution may also be a further cleanser which acts on the object with or without ultrasonic vibrations. Thereafter, in step 59, controller 30 opens locking pin 17. The user can then remove object 20 at any time. Controller 30 may optionally illuminate an LED to indicate that the cleaning cycle is completed.

Cleaning solution 19 may include a mild acidic cleaning solution, a disinfectant, a detergent or a combination of these or other components. Ideally, dentures are cleaned by soaking them in a mild acidic cleaning solution and then subjecting them to ultrasonic vibrations. However, this could not be practically performed in a residential home, because of the risk that the dentures would be taken out of the mild acidic cleaning solution and placed directly into the user's mouth. Controller 30 of the present invention keeps cleaning tank 14 locked so that the dentures cannot be removed until the mild acidic cleaning solution has been rinsed off. Rinse solution 13 is a mouthwash solution or a further non-toxic cleaning solution for the dentures. Rinse solution 13 rinses the cleaning solution 19 off object 20 and dilutes any residual acid solution to a safe level.

Steps 57, 58 and 59 from FIG. 2 indicate that cleaning solution 19 is drained from cleaning tank 14 and that subsequently rinse solution 13 is introduced into cleaning tank 14. An alternative procedure would be to open cleaning tank valve 18 to drain cleaning solution 19 and thereafter keeping valve 18 open while a small amount of rinse solution 13 rinses object 20 and washes any residual sediment out of tank 14. Thereafter, valve 18 would be closed and the remainder of rinse solution 13 would be introduced into cleaning tank 14. In a further embodiment, cleaning solution 19 is drained from cleaning tank 14 and then one half of rinse solution 13 is introduced into cleaning tank 14. This rinse solution is then discharged into waste tank 27 and the remaining half of rinse solution 13 is then drained into cleaning tank 14.

If at any time the user wishes to interrupt the cleaning cycle, cycle selectors 31 and 32 can be depressed simultaneously, for example, and the cleaning solution will be drained from cleaning tank 14, object 20 will be rinsed with rinse solution 13 and cleaning tank locking pin 17 will be deactivated within a very short period of time. In other words, if the user interrupts the cycle, object 20 will be subjected to a quick rinse to that the object can be quickly removed from cleaning tank 14. Rinse solution 13 will be selected to properly hydrate acrylic and soft reline materials of dentures. The rinse material may also include added flavoring agents, i.e. mouthwash, to provide a refreshing taste when the dentures are placed into the user's mouth.

While object 20 is being soaked and subjected to ultrasonic vibrations, sediment and other particles may be dislodged from the object. This sediment will fall through screen 25 which will have openings appropriately sized to support object 20. The sediment which passes through screen 25 collects on drain plate 24 away from object 20. Drain plate 24 is sloped downwardly toward cleaning tank valve 18 to facilitate the removal of the sediment from cleaning tank 14 when either the cleaning liquid or the rinse liquid is drained from tank 14 through valve 18.

Cleaning apparatus 8 may optionally include multiple tanks 14 for institutional use where it is desirable to clean many sets of dentures simultaneously. Alternatively, multiple baskets may be provided, and individually labelled, to separate the sets of dentures which are cleaned in a single or multiple tanks 14. FIG. 3 shows a perforated basket or box 70.

While a single embodiment of the present invention has been shown and described, it is to be understood that many changes and modifications may be made thereunto without departing from the spirit and scope of the invention as defined in the appended claims.

What is claimed is:

1. An apparatus for cleaning an object in a cleaning solution and rinsing the object in a rinse solution, comprising:
   a cleaning tank adapted to receive the object and the cleaning solution, the cleaning tank having an inlet valve and an outlet valve;
   a storage tank coupled to said inlet valve for storing the rinse solution;
   a removable waste tank disposed below said outlet valve for receiving solution from said cleaning tank, said waste tank being separable from a remainder of the apparatus to discard the solution contained therein;
   an ultrasonic transducer coupled to said cleaning tank for generating ultrasonic vibrations in said cleaning solution;
   a controller including timing means coupled to said inlet valve, said outlet valve and said ultrasonic transducer, said timing means
      maintaining said object immersed in said cleaning solution for a first predetermined period of time, and
      generating ultrasonic vibrations in said cleaning tank for a second predetermined period of time;
   said controller thereafter opening said outlet valve to drain said cleaning solution from said cleaning tank into said waste tank and then closing said outlet valve; and
   said controller subsequently opening said inlet valve to drain rinse solution from said storage tank into said cleaning tank.

2. The apparatus according to claim 1, wherein said cleaning solution is selected from a group consisting of a mild acidic cleaning solution, a disinfectant and a detergent.

3. The apparatus according to claim 2, wherein said cleaning tank has a cleaning tank lid and a lock for locking said lid in a closed position, said lock being coupled to said controller, whereby said controller maintains said lid locked until said cleaning tank is filled with the rinse solution.

4. The apparatus according to claim 3, wherein said rinse solution and said cleaning solution are selected to properly hydrate acrylic denture material and soft reline materials.

5. The apparatus according to claim 4, wherein said controller comprises a microprocessor having input means for selecting different cleaning and rinse cycles.

6. The apparatus according to claim 5, additionally comprising a perforated basket to contain and identify the object within said cleaning tank.

7. An apparatus for soaking and cleaning dentures in a mild acidic cleaning solution and rinsing the dentures in a rinse solution, the apparatus comprising:
   a cleaning tank having a cleaning tank cover, an inlet valve and an outlet valve, said cleaning tank being adapted to contain the dentures and the mild acidic cleaning solution;
   locking means for locking said cleaning tank cover closed onto said cleaning tank;
   a storage tank disposed generally above said cleaning tank and coupled to said inlet valve, said storage tank being adapted to contain the rinse solution;
   a removable, drawer-type waste tank disposed below said outlet valve;
   an ultrasonic transducer coupled to said cleaning tank for generating ultrasonic vibrations in said cleaning solution;
   control and timing means coupled to said inlet valve, said outlet valve, said locking means, and said ultrasonic transducer, said control and timing means activating said locking means to lock said tank cover closed while soaking the dentures in the mild acidic cleaning solution for a first predetermined period of time and generating ultrasonic vibrations in the mild acidic cleaning solution for a second predetermined period of time;
   said controller and timing means thereafter opening said outlet valve to drain the mild acidic cleaning solution from said cleaning tank into said removable, drawer-type waste tank and then closing said outlet valve;
   said controller and timing means subsequently opening said inlet valve to drain the rinse solution from said storage tank into said cleaning tank;
   wherein said controller and timing means deactivates said locking means once the mild acidic cleaning solution is rinsed off the dentures and diluted to a safe level;
   said controller and timing means finally draining the rinse solution into said drawer-type waste tank; and
   said drawer-type waste tank being removable from a remainder of the apparatus to empty the solution contained therein.

* * * * *